United States Patent
Davis et al.

(10) Patent No.: US 11,819,239 B2
(45) Date of Patent: *Nov. 21, 2023

(54) MACERATING AND ASPIRATION TOOL FOR INTRACRANIAL SURGERY

(71) Applicant: Rebound Therapeutics Corporation, Irvine, CA (US)

(72) Inventors: Peter G. Davis, Irvine, CA (US); Ross Tsukashima, Irvine, CA (US); Jeffrey J. Valko, Irvine, CA (US); Todd D. McIntyre, Irvine, CA (US); Michael R. Henson, Irvine, CA (US)

(73) Assignee: Rebound Therapeutics Corporation, Irvine, CA (US)

(*) Notice: Subject to any disclaimer, the term of this patent is extended or adjusted under 35 U.S.C. 154(b) by 428 days.

This patent is subject to a terminal disclaimer.

(21) Appl. No.: 17/201,207

(22) Filed: Mar. 15, 2021

(65) Prior Publication Data

US 2021/0196311 A1 Jul. 1, 2021

Related U.S. Application Data

(63) Continuation of application No. 15/729,510, filed on Oct. 10, 2017, now Pat. No. 10,945,758.

(60) Provisional application No. 62/405,802, filed on Oct. 7, 2016.

(51) Int. Cl.
*A61B 18/12* (2006.01)
*A61B 17/3207* (2006.01)
*A61B 17/22* (2006.01)
*A61F 7/12* (2006.01)
*A61B 18/14* (2006.01)
*A61B 18/00* (2006.01)
*A61B 17/00* (2006.01)

(52) U.S. Cl.
CPC .. *A61B 17/320783* (2013.01); *A61B 17/2202* (2013.01); *A61B 17/320758* (2013.01); *A61B 18/1206* (2013.01); *A61B 18/1492* (2013.01); *A61F 7/12* (2013.01); *A61B 2017/00057* (2013.01); *A61B 2017/22079* (2013.01); *A61B 2018/00404* (2013.01); *A61B 2018/00446* (2013.01); *A61B 2018/00577* (2013.01); *A61B 2018/00595* (2013.01); *A61F 2007/126* (2013.01)

(58) Field of Classification Search
CPC .............. A61B 17/221; A61B 17/2202; A61B 17/320783; A61B 17/320758; A61B 18/1206; A61B 18/1492; A61B 2018/00404; A61B 2018/00577
See application file for complete search history.

(56) References Cited

U.S. PATENT DOCUMENTS

| | | |
|---|---|---|
| 5,823,990 A | 10/1998 | Denley |
| 6,610,059 B1 | 8/2003 | West, Jr. |
| 9,968,249 B2 | 5/2018 | Huang et al. |
| 2002/0095100 A1 | 7/2002 | Lee et al. |
| 2003/0097129 A1 | 5/2003 | Davison et al. |
| 2005/0165345 A1 | 7/2005 | Laufer et al. |
| 2009/0281540 A1 | 11/2009 | Blomgren et al. |

FOREIGN PATENT DOCUMENTS

WO WO2016053778 4/2016

*Primary Examiner* — Daniel W Fowler
(74) *Attorney, Agent, or Firm* — Crockett & Crockett, PC; K. David Crockett, Esq.

(57) ABSTRACT

A macerating and aspiration tool for removing blood masses from the brain.

12 Claims, 6 Drawing Sheets

Fig. 1
Fig. 1A
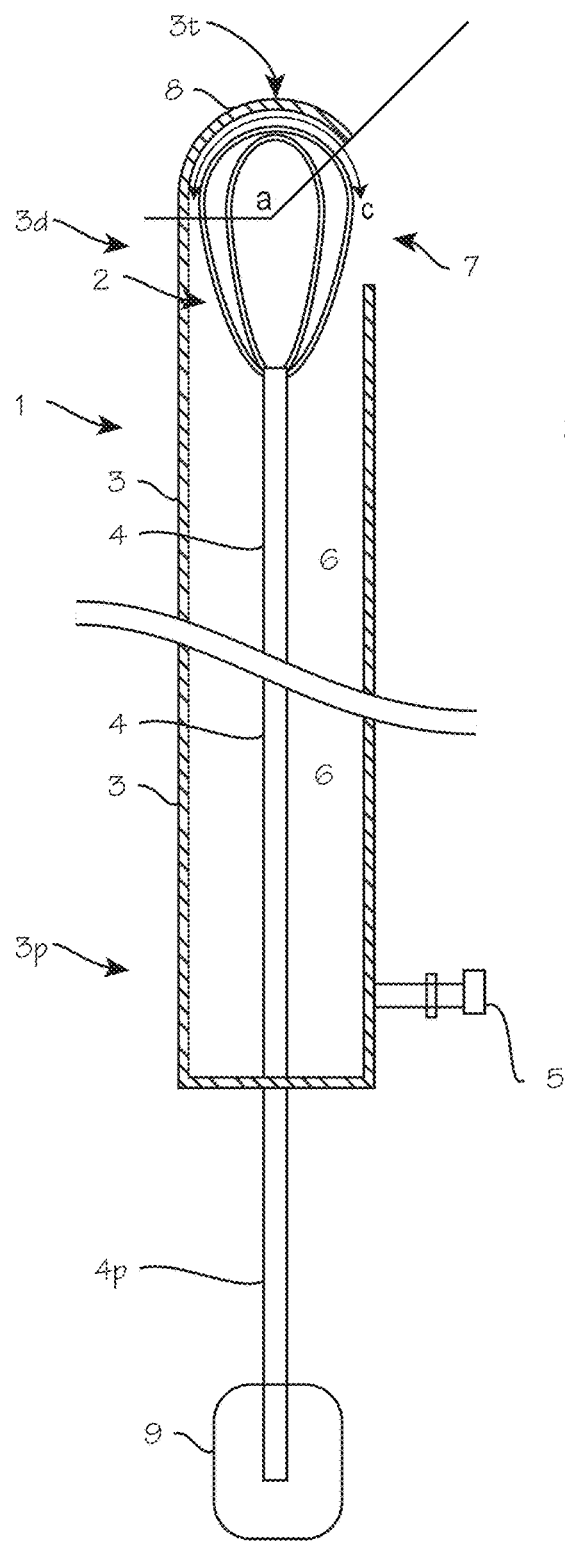
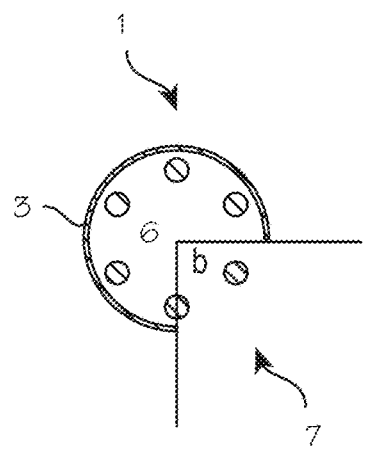

MACERATING AND ASPIRATION TOOL FOR INTRACRANIAL SURGERY

This application is a continuation of U.S. application Ser. No. 15/729,510, filed Oct. 10, 2017, now U.S. patent Ser. No. 10/945,758, which claims priority to U.S. Provisional Application 62/405,802, filed Oct. 7, 2016, now expired.

FIELD OF THE INVENTIONS

The inventions described below relate to the field of minimally invasive brain surgery.

SUMMARY

The devices and methods described below provide for rapid removal of a blood mass from the brain while minimizing the potential for damage to healthy brain tissue surrounding the blood mass and the device. The device includes a rotating macerating structure, shaped like a wire whisk or egg beater, disposed within the distal end of a tube. A side aperture in the tube, longitudinally aligned with the macerating structure, allows for fluid communication between the lumen of the tube and the blood mass proximate the exterior of the tube distal end. The macerating structure is rotatable within the tube, with a drive rod fixed to the macerating structure and extending proximally to the proximal end of the tube. The rod may be rotated manually, or with a motor, to macerate the blood mass, and suction may be applied to the tube while the macerating structure is rotating, to quickly remove the blood mass.

BRIEF DESCRIPTION OF THE DRAWINGS

FIGS. 1 and 1A illustrate a macerating and aspiration tool for intracranial surgery through an opening in the skull.

DETAILED DESCRIPTION OF THE INVENTIONS

Figure 2:
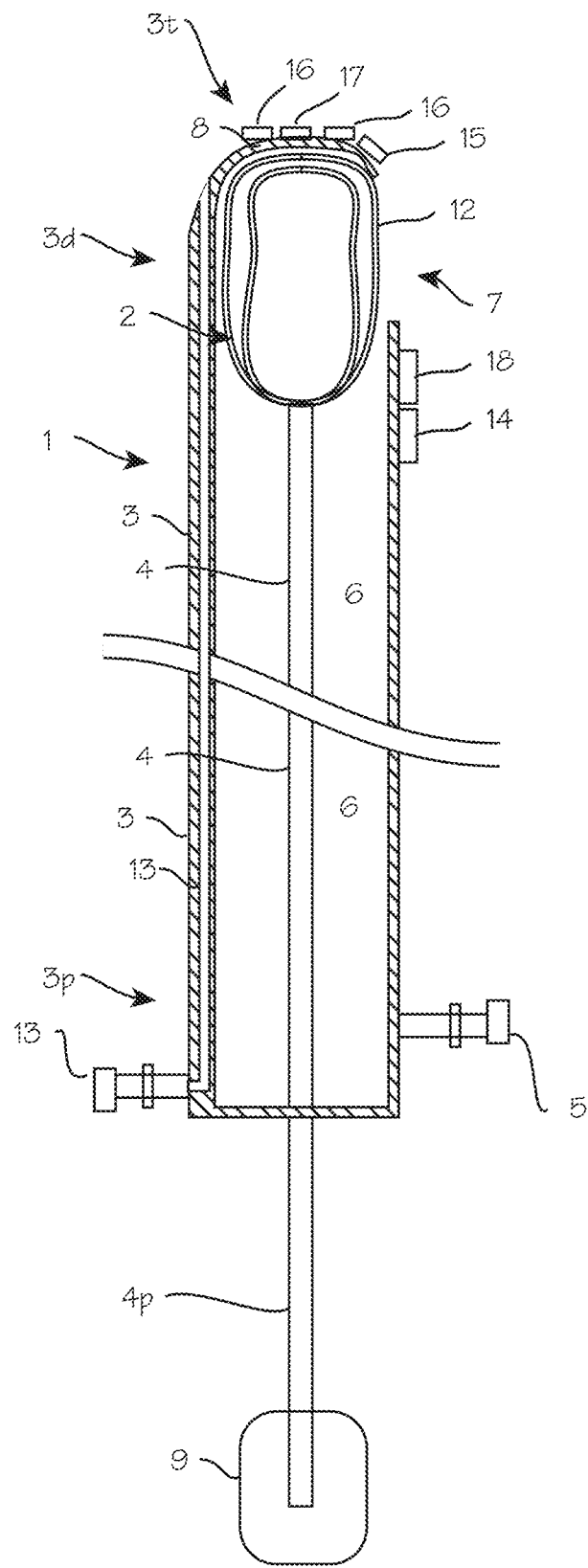
FIG. 2 illustrates a new multi-function tool for intracranial surgery through an opening in the skull.

FIGS. 1 and 1A illustrate a new macerating and aspiration tool 1 for intracranial surgery through an opening in the skull. The tool comprises, primarily, a macerating structure which in this The macerating structure in this tool comprises a wire basket or cage in the form of a rotatable wire whisk 2, rotatably disposed with the tip of a tube 3, along with a rod 4 secured to the whisk for rotating the whisk, and a suction port 5 for connection to a vacuum source. The tube 3 is characterized by a distal end 3d, intended for insertion into the brain, and a proximal end 3p, which in use will remain outside the brain, and a lumen 6. At the distal end, the tube is closed, with the exception of a side-facing aperture 7 longitudinally proximate the wire whisk 2. The distal tip 3t of the tube is closed or hooded, with a cap or hood 8 having a rounded or semispherical outer contour, as shown, or a pointed conical outer contour. The inner contour of the closed distal end of the tube is rounded, or bowl-shaped, to match the round contour of the distal-facing portion of the wire whisk. The wire whisk is secured to the distal end 4d of the rod 4, which extends proximally through the tube, such that its proximal end 4p may be rotated by a actuator 9 (which may be a motor or manually operated trigger (such as the SPINR device) or by hand, by a surgeon placing the device. The vacuum port 5 is disposed at the proximal end of the tube, in fluid communication with the lumen 6 of the tube. In use this port is to be secured to a vacuum source. In this structure, the lumen is only partially occupied by the slender rod 4, which has a diameter substantially smaller than the inner diameter of the tube and is preferably devoid of auger screw threads, or in any case devoid of auger screw threads with outer diameters closely matching the inner diameter of the tube, and no bushing or bearings or other structures are disposed within the lumen, between the suction port and the side facing aperture, leaving an un-occluded fluid pathway between the aperture and the suction port. The inner surface of the distal tip provides any necessary bearing surface for the rotating whisk. The whisk is preferably non-expandable, and sized to closely match the inner dimensions (the diameter and/or the contour) of the tube distal end or distal tip 3t and cap 8. The tube distal end, the distal tip, and the cap are all preferably non-expandable, with fixed outer dimensions. The side-aperture extends circumferentially around the tube, and longitudinally along the tube, to a limited extent, so that the whisk may not exit the tube during rotation. The depth of the cap, and the extent to which it covers the distal facing portion of the macerating structure, is sufficient, in combination with the extent of the aperture, to ensure that the macerating structure does not extend beyond the outer dimensions of the distal end of the tube. Preferably, the aperture is limited in circumferential extent (angle b in FIG. 1A) to less than 180°, to ensure that the macerating structure does not inadvertently contact healthy brain tissue on one side of the device while the surgeon is applying the other side of the device to a blood mass. Alternately, or in combination with the circumferential limit on the side aperture, the cap subtends an angle (angle a in FIG. 1) of at least about 135° spherically around the distal contour of the macerating structure (depicted by angle C in FIG. 1). Where contact with brain tissue on the back side (opposite the blood mass) is not a concern, the aperture may be wider, and multiple apertures may be provided, and the cap may be characterized as a bowl-shaped hood secured to the distal end of the tube with one or more posts extending distally from the distal end of the tube.

FIG. 2 illustrates a new multi-function tool for intracranial surgery through an opening in the skull. This tool 11 is similar to the tool 1 illustrated in FIG. 1, and includes the tube 3, the rod 4, the suction port 5 in fluid communication with the lumen 6 and the side facing aperture 7 providing for fluid communication between the lumen and the exterior of the tube distal tip. The macerating structure in this tool comprises a wire basket 12, with wires having a rounded square configuration, such that the overall structure of the macerating structure is comparable to egg beater blades of a hand-held food mixer. In other aspects, the device of FIG. 2 incorporates the features described in relation to the device of FIG. 1. In both configurations, dimensions of the macerating structure may be chosen to minimize obstruction to the application of suction to the blood proximate the aperture and minimize resistance to flow of macerated tissue proximally through the device.

The macerating structures of FIGS. 1 and 2 may be comprised of any number of wires, preferable two to eight wires, in a tear-drop configuration to make up the wire whisk, or in a rounded square configuration to make up the egg-beater configuration. The macerating structure is preferably 3 to 15 mm long, 0.5 to 5 mm in outer diameter, constructed with wires 0.05 to 0.5 mm in diameter (or max width), and the rod is preferable 0.25 to 1 mm in diameter, while the inner diameter of the tube is preferably 0.5 to 2 mm. With these dimensions, the macerating structure may be rotated at a rate of 200 to 4000 rotations be minute, and vacuum may be applied in the range of 6,666 to 66,666 Pa (50 to 500 mmHG).

FIG. 2 also illustrates various additional features which may be combined with the device of FIG. 1 or FIG. 2, and may be combined alone or in combination, to achieve the beneficial aspects of each feature with or without the beneficial aspects of other features. As shown in FIG. 2, the device may include a fluid supply port 13, which opens on the main lumen 6, or a side lumen 14 in the wall of the tube 3, which can be connected to a source of lytic fluid (streptokinase, urokinase, heparin, factor VII, TPA, etc.). Lytic fluids may flow through the main lumen 6 and out of the aperture 7, or through a side lumen 14 and out of an opening in the side lumen located at the distal end of the tube. The device may also include an ultrasound transmitter 15 proximate the distal tip, and operable to emit ultrasound into the blood mass to aid in lysis, or heating elements, also operable to heat the blood mass and promote lysis in combination with the lytic agents. The fluid supply port may also be used to inject saline, TPA or other fluids into the site of the blood mass, for breaking down the blood mass, lysis, or oxygenating surrounding tissue. The outer surface of the tube may be covered with a non-reflective or anti-glare coating, or a black or flat black coating (heat-shrink tubing, paint or powder coat), or may be made of non-reflective or anti-glare coating, or a black or flat black, to avoid creating glare when used in combination with our intracranial cannula with a rim-mounted camera.

The device may also include ablation electrodes 16 disposed on the distal end of the device, on the distal facing surface of the cap 8, as shown, or on a side facing surface of the cap, coupled to an RF generator, which can be operated to apply RF energy to cauterize bleeding blood vessels encountered while clearing a blood mass from the brain. The electrodes may be activated manually, by a surgeon operating the RF generator, or they may be activated by a pressure switch 17 disposed between the electrodes.

The device may also include a camera or color sensor 18, according to our co-pending application 62/337,498, filed May 17, 2016, for detecting the color of tissue surrounding the distal tip of the device, and an LED 19 for providing illumination needed for the color sensor or for direct visualization by the surgeon using the device, or an image sensor (camera) disposed at the distal end of the tip of the device.

Figure 3:
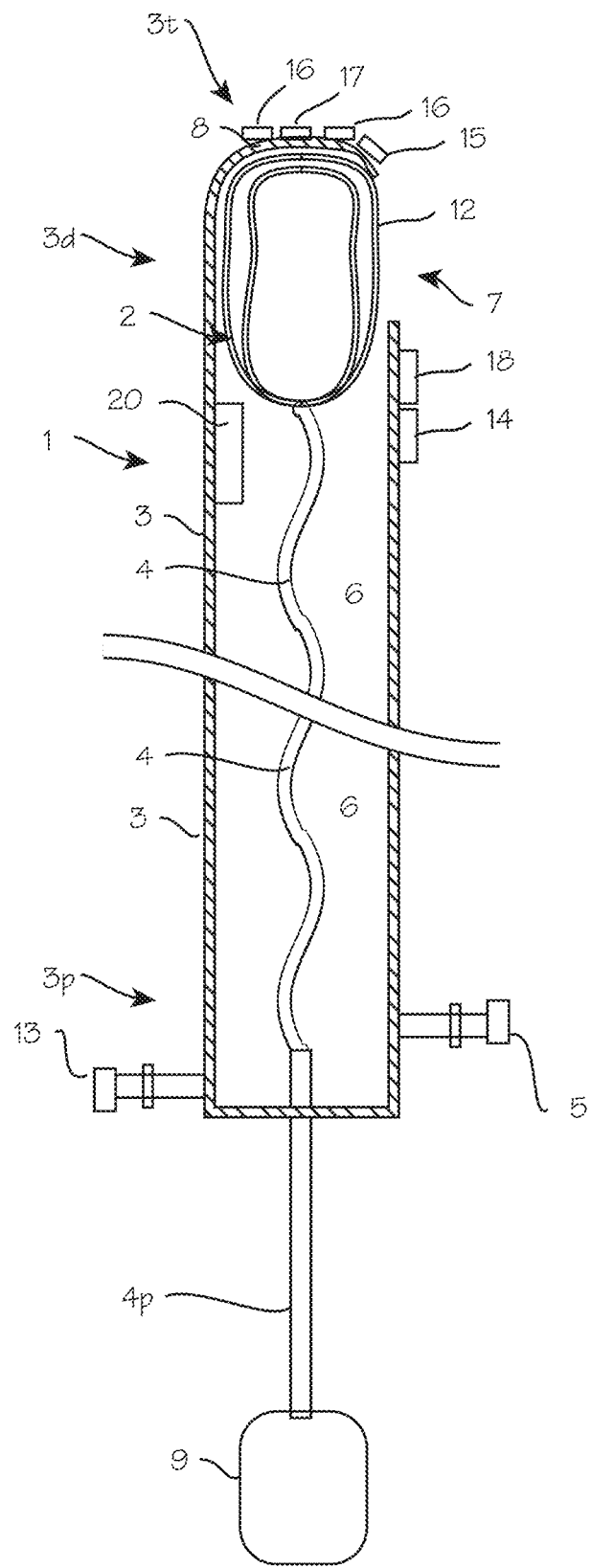
FIG. 3 illustrates a macerating and aspiration tool of FIG. 1 with a drive rod configured to prevent clogging of the device.

As shown in FIG. 3, the rod 4 may be helical, to provide, during rotation of the rod, agitation of any blood mass drawn into the tube, and thus assist in aspiration and prevent clogging of the tube. Additional modifications may be included. The tube may be straight, or a straight helix, as depicted, curved or bent toward the distal end to accommodate different approaches to a blood mass, and the drive rod may be flexible, or jointed, to accommodate the bend, with a joint or flexible coupling (for example, wound drive shaft portion) disposed longitudinally proximate the bend in the tube. Also, the drive rod may be longitudinally fixed relative to the outer tube, so that the macerating structure cannot translate longitudinally relative to the window, or it may be translatable, relative to the tube, so that the macerating structure may be translated longitudinally, and axially reciprocated back and forth within the tube, to assist in drawing portions of the blood mass into the tube.

Figure 4:
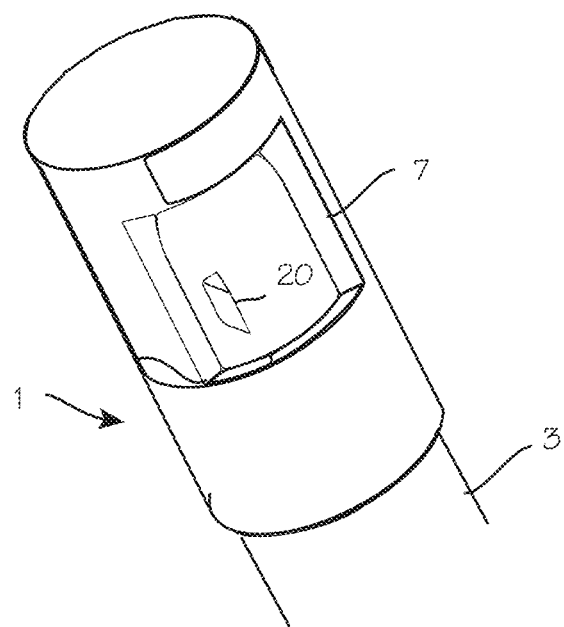
FIG. 4 illustrates a macerating and aspiration tool of FIG. 1 with a means for severing fibrous portions of a blood mass within the tool.

FIG. 4 illustrates a macerating and aspiration tool of FIG. 1 with a means for severing fibrous portions of a blood mass within the tool. The means for severing fibrous portions comprises a cutter 20, disposed on the inner wall of the tube and protruding radially inwardly toward the rod, just proximal to the macerating structure (as seen in FIG. 3). This cutter may comprise a flat piece or wedge, protrudes toward the rod, and functions to break up any fibrous tissue drawn into the lumen, to prevent fibrous tissue from gathering on the rod and obstructing the evacuation passage provided by the lumen. The cutter may be employed in the devices of FIG. 1, 2 or 3.

Figure 5:
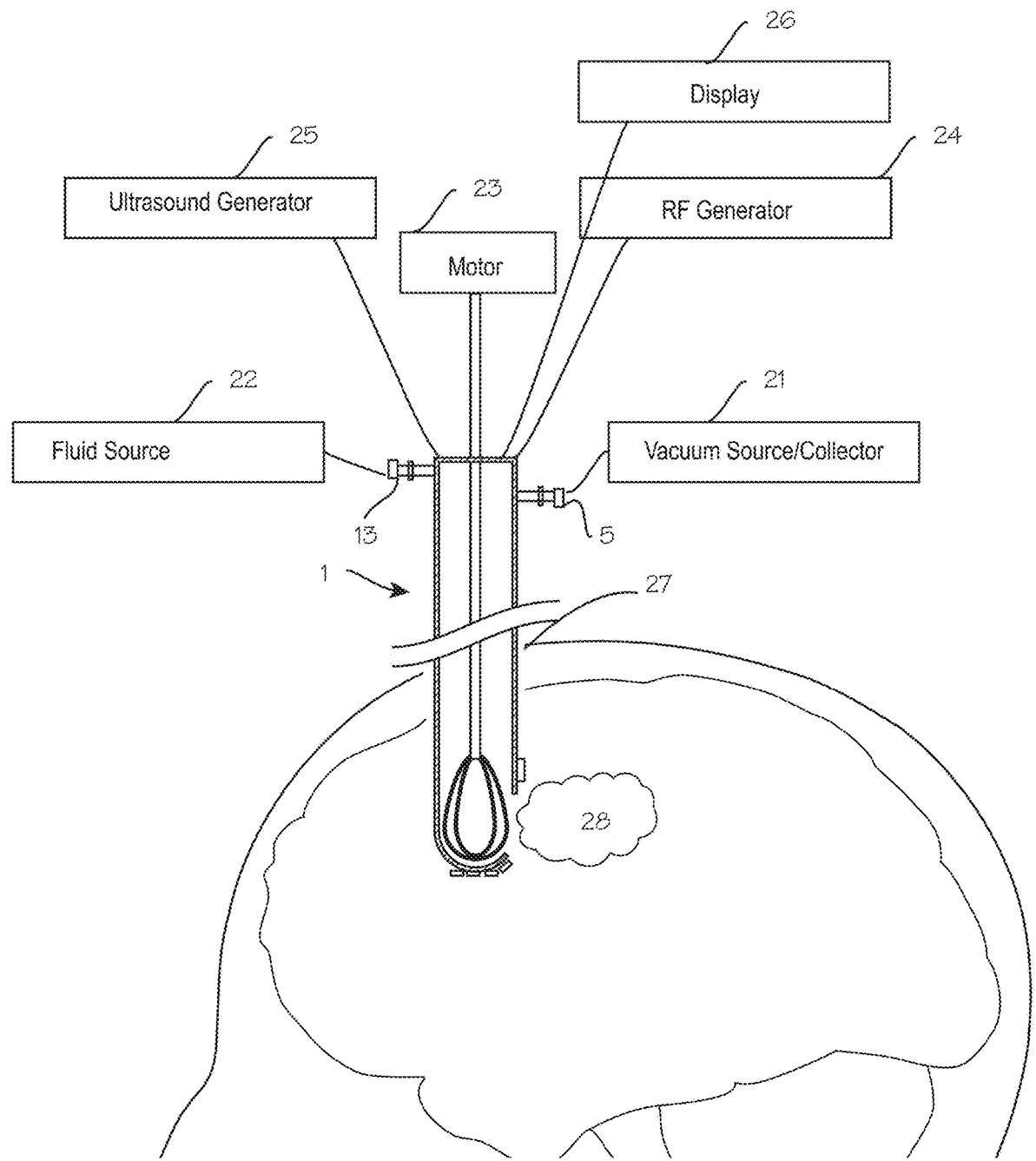
FIG. 5 illustrates the device and the system in which it is used.
Figure 6:
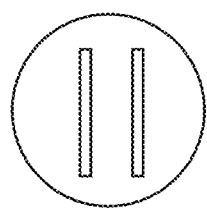
FIGS. 6 through 10 illustrate various configurations of distally facing electrodes disposed on the distal tip of the tool.
Figure 7:
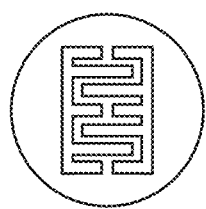
Figure 8:
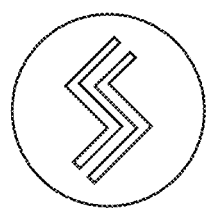
Figure 9:
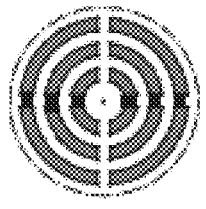
Figure 10:
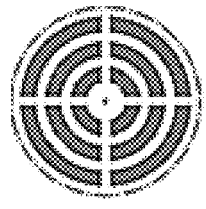

The device described in the previous figures is intended for use in the system depicted in FIG. 5. As shown in FIG. 5, the system includes the macerating and aspiration tool 1, with the suction port 5 in fluid communication to a vacuum source 21 and waste collector, and the fluid supply port 13 in fluid communication with a fluid source 22 (and, if necessary, a pump to pump fluids through the port and the tube and into the site of the blood mass. A motor 23 is operable connected to the rod 4, though a manual trigger may be used in lieu of a motor, or the proximal end of the rod may terminate in a free end which can be twisted manually by the surgeon operating the device. Where RF cautery electrodes, ultrasound transducers, or heating elements are provided in the device, an RF generator 24, ultrasound generator 25, or heating power supply can is provided in the system. If a color sensor or other sensor is provided in the device, and associated display 26 is provided. For ease of operation, a handle may be fixed to the proximal end. The various functions of whisk/beater rotation, application of suction, injection of fluids, application of RF energy, ultrasound or heating, may be controlled with switches or buttons on the handle, on the respective actuator device, control boxes, and power sources, or on an associated foot switches.

Thus, the device for removing a blood mass from the brain comprises a tube having a distal end and a proximal end and a lumen having a diameter, extending from the distal end to the proximal end, said tube having a cap covering or enclosing the distal end of the tube, and a side aperture disposed on the distal end of the tube, said side aperture communicating from the lumen to the outside of the tube distal end. A suction port is disposed on the proximal end of the tube, in fluid communication with the lumen, and a macerating structure is disposed within the lumen, longitudinally aligned with the side aperture. A drive rod is rotationally fixed to the macerating structure, with the drive rod extending proximally from the macerating structure to the proximal end of the tube. The drive rod is rotatable from the proximal end of the tube to cause rotation of the macerating structure and has a small diameter relative to the diameter of the lumen (the inner diameter of the tube) so that together, the inner tube and rod provide an annular lumen for aspiration of macerated tissue from the blood mass through the tube. The system in which the device is used comprises the vacuum source. The device may optionally include any or all of the additional features described in reference to FIG. 2, and the corresponding system may include the corresponding fluid source, power sources, or display as illustrated in FIG. 4.

FIGS. 6 through 10 illustrate various configurations of distally facing electrodes disposed on the distal tip of the tool, in embodiments where RF cautery electrodes are provided on the device. The electrodes are provided on the distal tip of the device, preferably on the distally facing surface, and may be used to cauterize bleeding blood vessels (perhaps uncovered while removing the blood mass) by pressing the electrodes against a bleeding vessel and operating the RF generator to apply RF energy to the vessel through the electrodes. The electrodes may be side-by-side electrodes shown in FIG. 6, the electrodes with interdigitating segments as shown in FIG. 1, the nested zig-zag or S-shaped electrodes of FIG. 8, or the concentric semicircular or quarter-circular electrodes of FIG. 9 or 10.

In use, a surgeon will insert the device into the brain of a patient, through a burr hole or craniotomy/craniectomy opening 27 in the skull of the patient, and perhaps through a previously placed intracranial cannula, until the distal end and side aperture are proximate a blood mass 28, with the macerating structure exposed to the blood mass through the side aperture. With the side aperture facing the blood mass, the surgeon will rotate the whisk/beater by energizing the motor, or operating the trigger of the trigger mechanism, or twisting the proximal end of the rod by hand. The surgeon will also operate the vacuum source, to apply suction to the tube, while rotating the whisk/beater or alternatingly applying suction, rotating the whisk/beater repeatedly.

During use, the surgeon will rotate the macerating structure at a rate of up to 4000 rotations per minute using a motor, or rotate the macerating structure slowly by hand, and apply vacuum may be applied in the range of 6666 to 66666 Pa (50 to 500 mmHG). These parameters provide for rapid evacuation of coagulated blood masses, while minimizing the potential to disrupt healthy brain tissue. These parameters may be varied, as clinical experience dictates, for intracranial use or for use in other procedures in other areas of the body.

Optionally, the surgeon may inject fluids through the fluid supply port (or connecting a fluid supply to the vacuum port and injecting fluids through the vacuum port), apply ultrasound energy to the blood mass, or heat the blood mass with the heating elements. If cautery electrodes are provided on the tip of the device, the surgeon will, upon encountering a bleeding blood vessel during the course of aspirating the blood mass, manipulate the device to place the electrodes in contact with the blood vessel, and operate the RF generator to apply energy to the blood vessel and cauterize the blood vessel. When the surgeon is satisfied that the blood mass has been adequately removed, the surgeon will remove the device and close the skull, or install a drain, as indicated for the particular patient's condition.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method for extracting a blood mass from the brain of a patient, said method comprising:
   providing a device for removing a blood mass from the brain, said device comprising:
   a tube having a distal end and a proximal end and a lumen having a diameter, extending from the distal end to the proximal end, said tube having a cap enclosing the distal end of the tube, and a side aperture disposed on the distal end of the tube, said side aperture communicating from the lumen to the outside of the tube distal end;
   a suction port disposed on the proximal end of the tube, in fluid communication with the lumen;
   a macerating structure disposed within the lumen, longitudinally aligned with the side aperture, and a drive rod rotationally fixed to the macerating structure, said drive rod extending proximally from the macerating structure to the proximal end of the tube, said drive rod being rotatable from the proximal end of the tube to cause rotation of the macerating structure; wherein
   the drive rod has a small diameter relative to the diameter of the lumen (the inner diameter of the tube), and together with the tube provide an annular lumen for aspiration of macerated tissue from the blood mass through the tube; wherein
   the cap has an inner surface, distal to the side aperture, configured to provide a bearing surface for the macerating structure;
   inserting the distal end of the tube into the brain, until the distal end of the tube is proximate the blood mass and the macerating structure is exposed to the blood mass through the side aperture; and
   rotating the macerating structure while applying suction to the tube through the suction port, to extract the blood mass from the brain.

2. The method of claim 1, wherein:
   the device is provided in a form wherein the macerating structure comprises a cage, having a round distal contour, and the cap has a rounded inner surface.

3. The method of claim 1, wherein:
   the device is provided in a form wherein the macerating structure comprises a cage, having a round distal contour, and the cap has a rounded inner surface.

4. The method of claim 1, wherein: the device is provided in a form wherein the macerating structure comprises a wire whisk, having a round distal contour, and the cap has a rounded inner surface.

5. The method of claim 1, wherein: the device is provided in a form wherein the macerating structure comprises a wire basket, with wires having a rounded square distal contour, and the cap has a rounded square inner surface.

6. The method of claim 1, wherein: the device is provided in a form further comprising means for severing fibrous tissue, disposed within the lumen of the tube for severing fibrous tissue within the tube.

7. The method of claim 1, wherein: the device is provided in a form wherein the means for severing fibrous tissue comprises a cutter, disposed on an inner wall of the tube and protruding radially inwardly toward the rod, proximal to the macerating structure.

8. The method of claim 1, wherein: the device is provided in a form wherein the macerating structure is non-expandable, and sized to closely match an inner diameter of the tube distal end.

9. The method of claim 1, wherein: the device is provided in a form wherein the macerating structure is non-expandable, and sized to closely match an inner contour of the cap.

10. The method of claim 1, wherein: the device is provided in a form wherein the side aperture extends circumferentially around the distal end of the tube, less than 180°.

11. The method of claim 1, wherein: the device is provided in a form wherein the cap extends at least 135° spherically around the distal contour of the macerating structure.

12. The method of claim 1, wherein: the device is provided in a form wherein the side aperture is formed by a space defined between the cap and one or more posts extending distally from the distal end of the tube to fix the cap to the distal end of the tube.

* * * * *